US006395782B1

(12) United States Patent
Cook et al.

(10) Patent No.: US 6,395,782 B1
(45) Date of Patent: May 28, 2002

(54) METHOD OF INCREASING LONGEVITY AND PREVENTING BODY WEIGHT WASTING IN AUTOIMMUNE DISEASE BY USING CONJUGATED LINOLEIC ACID

(75) Inventors: Mark Cook; Ming-der Yang; Michael W Pariza, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/798,063

(22) Filed: Mar. 2, 2001

(51) Int. Cl.$^7$ .............................................. A61K 31/20
(52) U.S. Cl. ...................................................... 514/560
(58) Field of Search ......................................... 514/560

(56) References Cited

U.S. PATENT DOCUMENTS

| | | | |
|---|---|---|---|
| 4,328,243 A | 5/1982 | Horrobin et al. | 424/301 |
| 5,428,072 A | 6/1995 | Cook et al. | 514/560 |
| 5,430,066 A | 7/1995 | Cook et al. | 514/558 |
| 5,444,054 A | 8/1995 | Garleb et al. | 514/54 |
| 5,554,646 A | 9/1996 | Cook et al. | 514/560 |
| 5,585,400 A | 12/1996 | Cook et al. | 514/560 |
| 5,674,901 A | 10/1997 | Cook et al. | 514/558 |
| 5,725,873 A | 3/1998 | Cook et al. | 424/442 |
| 5,760,083 A | 6/1998 | Cook et al. | 514/560 |
| 5,814,663 A | 9/1998 | Cook et al. | 514/560 |
| 5,855,917 A | 1/1999 | Cook et al. | 424/502 |
| 5,914,346 A | 6/1999 | Cook et al. | 514/558 |
| 5,919,451 A | 7/1999 | Cook et al. | 424/130.1 |
| 6,020,376 A | 2/2000 | Pariza et al. | 514/558 |
| 6,020,378 A | 2/2000 | Cook et al. | 514/560 |

OTHER PUBLICATIONS

Cook et al. Abstract Paper—Am. Chemical Society (2000), 220th, AGFD–010.*
Chew et al., Effects of Conjugated Dienoic Derivatives of Linoleic Acid and β–Carotene in Modulating Lymphocyte and Macrophage Function, *Anticancer Research* 17: 1099 (1997).
Chin et al., "Conjugated Linoleic Acid is a Growth Factor for Rats as Shown by Enhanced Weight Gain and Improved Feed Efficiency" *J. Nutri* 124: 2344–2349 (1994).
Cook et al., "Exogenous Antigen Challenge and Its Effect on Nutrient Metabolism," *Proceedings American Association of Swine Practitioners* 25$^{th}$ Annual Meeting (1994).
Cook et al., "Immune Modulation by Altered Nutrient Metabolism: Nutritional Control of Immune–Induced Growth Depression, Symposium: The Microenvironment of Immune Tissue," *Poultry Science* 72: 1301–1305 (1993).

Fernandes et al., "Increased TFG–β and Decreased Oncogene Expression by ω–3 Fatty Acids in the Spleen Delays Onset of Autoimmune Disease in B/W Mice," *J. Immunol.* 152: 5979 (1994).
Hayek et al., "Dietary Conjugated Linoleic Acid Influences the Immune Response of Young and Old C57BL/6NCrIBR Mice," *J. Nutri.* 129: 32–38 (1999).
Kumar et al., "Effect of n–6 and n–3 Fatty Acids on the Proliferation of Human Lymphocytes and Their Secretion of TNF–α and IL–2 In Vitro," *Nutrition Research* 12: 815–823 (1992).
Lambert et al., "Pathogenesis of the Glomerulonephritis of NZB/W Mice," *J. of Exp. Med.* 127: 507 (1968).
Miller et al., "Feeding Conjugated Linoleic Acid to Animals Partially Overcomes Catabolic Responses Due to Endotoxin Injection," *Biochemical and Biophysical Research Communications* 198: 1107–1112 (1994).
Pariza et al., "Conjugated Linoleic Acid (CLA) Reduces Body Fat," *FASEB Journal* 10: A560 (1996).
Park et al., "Effect of Conjugated Linoleic Acid on Body Composition in Mice", *Lipids* 32: 853–858 (1997).
Silvis, N., "Nutritional Recommendations for Individuals With Diabetes Mellitus," *South African Med. J.* 81: 162–166 (1992).
West et al. "Effects of Conjugated Linoleic Acid on Body Fat and Energy Metabloism in the Mouse," *Am. J. Physiol.* 275: R667–R672 (1998).
Weyman et al., "Linoleic Acid as an Immunosuppressive Agent," *Lancet* 2: 33 (1975).
Wong et al., "Effects of Dietary Conjugated Linoleic Acid on Lymphocyte Function and Growth of Mammary Tumors in Mice," *Anticancer Research* 17: 987–994 (1997).
Yang et al., "Dietary Conjugated Linoleic Acid Protects Against End Stage Disease of Systemic Lupus Erythematosus in the NZB/W F1 Mouse," *Immunopharmacology and Immunotoxicology* 22: 433–49 (2000).

* cited by examiner

*Primary Examiner*—Phyllis G. Spivack
(74) *Attorney, Agent, or Firm*—Quarles & Brady LLP

(57) ABSTRACT

Administering conjugated linoleic acid to human and non-human animals having conditions associated with the existence of autoimmune complexes or auto-immune reactive cells can extend the survival life time, prolong healthy tissue and organ function and prevent body weight wasting in these animals.

19 Claims, No Drawings

METHOD OF INCREASING LONGEVITY AND PREVENTING BODY WEIGHT WASTING IN AUTOIMMUNE DISEASE BY USING CONJUGATED LINOLEIC ACID

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

An autoimmune disease can be characterized by the presence of anti-self antibodies ("autoantibodies") or self-reactive B- and T-cell clones which are generally not observed in animals that do not have such a disease. The autoantibodies form immune complexes that become trapped in tissues and organs and thereby attract macrophages which can physically damage the animal's tissues or organs. For example, in the non-limiting case of a damaged kidney, protein molecules normally prevented from leaving the kidney in urine are instead excreted in the urine. A relatively common autoimmune disease is lupus, a chronic inflammatory disease that can affect various parts of the body, especially skin, joints, blood, and kidneys. More than 16,000 Americans develop lupus each year. It is estimated that 500,000 to 1.5 million Americans have been diagnosed with lupus.

Three types of lupus are known: systemic lupus (sometimes called systemic lupus erythematosus or "SLE"), discoid lupus, and drug-induced lupus. SLE can affect almost any organ or system of the body. Discoid lupus is always limited to the skin. Approximately 10 percent of discoid lupus evolve into the systemic form of the disease. Drug-induced lupus occurs after the use of certain prescribed drugs. The symptoms of drug-induced lupus are similar to those of systemic lupus. The symptoms usually fade when the medications are discontinued.

SLE is caused by defects in immune regulation that result in hyperactive T and B lymphocytes, which in turn causes widespread tissue damage by cell-mediated immune responses, autoantibodies or immune complexes. A hallmark of SLE pathogenesis is the presence of serum autoantibodies against nuclear components as a result of immune dysregulation. For example, IgG autoantibodies to DNA are responsible for the formation of immune complexes in SLE glomerulonephritis. Steward M W et al., *Clin. Exp. Immunol.* 26, 363 (1976); Lambert P H et al., *J. of Exp. Med.* 127, 507 (1968). The immune complexes are deposited along the wall in the small blood vessel of kidney, resulting in glomerulonephritis. About a third of patients with lupus develop nephritis which requires medical evaluation and treatment. Glomerular leakage of plasma proteins makes proteinuria an indicator of kidney damage by autoantibody immune complexes.

Conjugated linoleic acid ("CLA") is a group of positional and geometrical isomers of linoleic acid. Ha Y L et al., *Carcinogenesis* 8, 1881 (1987). These naturally occurring fatty acids are found in beef and dairy products due to ruminal isomerization of linoleic acid. Chin S F et al., *Journal of Nutrition* 124, 694 (1994). CLA has been shown to modulate immune response, Cook M E et al., *Poult. Sci.* 72, 1301 (1993); Chew B P et al., *Anticancer Res.* 17:1099 (1997); Miller C C et al., *Res. Commun.* 198, 1107 (1994), to reduce body fat, Park Y et al., *Lipids* 32, 853 (1997), and to have anti-carcinogenic and anti-atherosclerotic activity. Ha Y L et al., *Carcinogenesis* 8, 1881 (1987); Nicolosi R J et al., *Artery* 22, 266 (1997).

The active forms of UA include, in addition to the free acids, the active isomers of CLA; non-toxic salts thereof; active esters and other chemical derivatives thereof; and mixtures thereof.

Yang M et al., *Immunopharmacol Immunotoxicol.* 22(3), 433–49 (2000) studied the effects of CLA on SLE using a well-established animal model for SLE, namely NZB/W F1 mice. The model has been used for more than thirty years and was originally described by Lambert P H et al., J. of Exp. Med. 127, 507 (1968). NZB/W F1 mice are commercially available from Harlan-Sprague-Dawley (Madison, Wis.). Yang et al. reported that dietary CLA fed from weaning onward accelerates the onset of proteinuria but does not significantly affect anti-DNA antibody production in those same mice. In the same study, the CLA-fed mice lived longer from the onset of proteinuria and lost less body weight than control mice. Despite this, the total lifespan of CLA-fed animals did not differ from that of control animals, in view of the accelerated onset of the autoimmune disorders. The authors did not study effects of CLA on life span and body weight loss in animals other than those who were fed CLA for a lifetime, beginning at weaning and made no predictions about whether a similar effect might be observed in animals fed CLA at another stage of life or at another stage of the autoimmune disorder.

BRIEF SUMMARY OF THE INVENTION

In a first aspect, the invention is summarized in that a method for extending the survival time of a human or non-human animal having an autoimmune complex disease includes the step of administering to the animal after diagnosis of the autoimmune complex disease an amount of CLA effective to extend the life span of the animal.

In a related aspect, the invention is further summarized in that a method for reducing or preventing a body wasting effect in a human or non-human animal having an autoimmune complex disease includes the step of administering to the animal after diagnosis of the autoimmune complex disease an amount of CLA effective to reduce or prevent wasting of the animal.

It is an object of the invention to lessen the symptoms of an autoimmune disease on a human or non-human animal.

It is a feature of the invention that CLA can lessen the symptoms of an autoimrnune disease when administered after the effects of the disease on tissues and organs are observed.

Other objects, features and advantages will become apparent upon consideration of the following detailed description.

BRIEF DESCRIPTION OF THE SEVERAL VIEWS OF THE DRAWING

Not applicable.

BRIEF DESCRIPTION OF THE INVENTION

In general, the present invention provides methods for prolonging the life span and life of tissues and organs of a human or non-human animal and for preventing body weight wasting seen in human and non-human animals having an autoimmune disease at an advanced stage. Of particular note is treatment of conditions related to nephritis, or kidney tissue inflammation associated with various conditions including autoimmune conditions. Many of the conditions described herein can manifest themselves with nephritis symptoms. The method is applicable to all animals in which a disease state can result from undesired recognition of "self" and subsequent production of anti-self antibodies and anti-self immune cells. In particular, the method applies to human and non-human primates, other mammals, rodents and birds. The invention has particular application in the medical and veterinary fields.

Without intending to be limited to scientific theory, the applicants believe that the methods of the invention are effective because CLA can affect the production in the animal of prostaglandins and leukotrienes that can in turn reduce the ability of macrophages and related molecules to associate with autoantibodies to form the damaging immune complexes and cellular infiltrates. For purposes of this patent application, the methods are applicable whenever such immune complexes or inflammatory events exist and threaten an adverse effect on the animal. Because such immune complexes and cellular events are associated with increased permeability in the kidney to plasma proteins ("glomerular leakage"), protein in the urine ("proteinuria") is a convenient determinant of the disease stage at which the methods are appropriate, though it is possible to use other diagnostic techniques to confirm the presence of autoimmune complexes. For purposes of this application, the proteinuric condition is defined as protein in the urine at a level at or above about 1 mg/ml.

It should also be understood that cellular events of autoimmunity can result in damage to organs or tissues that is not associated with glomerular leakage. Such events include, but are not limited to, destruction of adrenal cells, lung basement membrane, thyroid, pancreatic beta cells, diethylcholine receptors, connective tissue and neural tissue.

The methods of the invention are not limited to use in human SLE patients (or equivalent diseases in non-human animals) but rather are suited for use in any animal where autoantibody immune complexes form and are deposited along the wall in the small blood vessels of the kidney and other tissues and organs resulting in tissue or organ disfunction. The methods are of particular use in other autoimmune diseases and conditions including but not limited to arthritis, multiple sclerosis, Addison's disease, Goodpastures's syndrome, Graves' disease, Hashimoto's thyroiditis, insulin-dependent diabetes mellitus, myasthenia gravis, myocardial infarction, poststreptococcal glomerulonephritis, spontaneous infertility, ankylosing spondylitis, rheumatoid arthritis, scleroderma, and Sjogren's syndrome. Because the effects of CLA in the claimed methods are attributed to an animal's ability to control the damaging effects of autoantibody immune complexes and immune reactive cells, rather than to the particularly underlying cause of an underlying autoimmune disease, CLA administered in accord with the methods of the invention has the same beneficial effects without regard to the identity of the underlying disease, as long as one manifestation of the underlying disease is the development of autoantibody immune complexes or self-immune reactive cells.

Proteinuria is merely a marker or symptom of the existence of such complexes. Other markers include, but are not limited to hormonal changes, tissue damage, and neurological dysfunction. In this example, administering CLA to an animal according to the methods, the time between onset of proteinuria and death is statistically longer and the animals exhibit less wasting and delayed organ damage than when an animal is not so treated. As is detailed in the example that follows, the effectiveness of the method is confirmed in a laboratory animal model (NZB/W F1 mice), as a prelude to actual testing in larger animals and humans. Since NZB/W F1 is a well established animal model for human SLE study, it is predicted that administering CLA to human patients having SLE and other immune diseases will have the same beneficial effects.

In the specific example shown below, 0.5% CLA in the diet was effective in prolonging the life span of the NZB/W F1 mice with proteinuria symptoms by 55%. The same level of CLA in the diet was also effective in reducing the body weight wasting in the NZB/W F1 mice with proteinuria symptom by 35%. However, 0.5% CLA in the diet is not the only effective dose. For example, it is expected that CLA from about 0.05% to about 2.0% in diet (or 0.1 to 10 g/day) will also produce beneficial effects to animals that suffer from autoimmune diseases and have developed proteinuria. It is also expected that the same range of about 0.05% to about 2.0% CLA in the diet (or 0.1 to 10 g/day) is effective to benefit humans and non-human patients who suffer from diseases having symptoms caused by autoimmune antibody complexes, including proteinuria. However, it should be noted that humans and non-human animals may not absorb CLA with equal efficiency. Therefore, to achieve the same beneficial effects in humans as those achieved in the animal model system, a higher or lower dose of CLA may be indicated.

Effects similar to those observed by the applicants can be observed using n-3 fatty acids in SLE patients and rodent models (Fernandes, G., et al., *J. Immunol.* 152:5979 (1994)). However, apart from the structural differences between the compounds, CLA is also about 20 times more effective than n-3 fatty acids in comparable methods. To have similar effects of 0.5% diet CLA, as described below, n-3 fatty acids would have to make up about 10% of the diet.

EXAMPLES

Methods

Materials. Conjugated linoleic acid (Natural Lipids Inc, Hovdebygda, Norway) contained 90% CLA (CLA-90) with the following C18:2 isomer distribution: 43.5% t10,c12, 41.9% c9,t11 and t9,c11, 1.5% t9,t11 and t10,t12, 0.9% c9,c11, 0.9% c10,c12. Other fatty acids in CLA-90 were 5.6% oleate, 1.4% palmitate, 0.5% linoleate, 0.4% stearate, and 3.4% unidentified compounds. All other chemicals and reagents were purchased from Sigma Chemical Co. (St. Louis, Mo.) unless specified.

Diet. Semi-purified powdered diet (TD94060, 99% basal mix, Harlan-Teklad, Madison, Wis.) was mixed with 0.5% oil (either CLA or corn oil) and 0.5% sucrose by weight, such that the final diet contained either 5.5% corn oil (control group) or 5% corn oil plus 0.5% CLA (CLA group) (Park Y et al., *Lipids* 32, 853 (1997)). Diets were prepared fresh every other week and stored at 4° C. Diets and water were provided ad libitum.

Animals. NZB/W F1, the offspring of New Zealand Black mice and New Zealand White mice, is a well-established animal model for human SLE study. (Lambert P H et al., *J. of Exp. Med.* 127, 507 (1968)). Twenty female NZB/W F1 mice were obtained at four weeks of age from Harlan-Sprague Dawley (Madison, Wis.) and housed in a temperature and humidity controlled room with 12 hour light/dark cycle. Two mice were housed in a cage and given a pelleted chow for a week before they were assigned to a control semi-purified diet. Mice were maintained on the semi-purified diet until they were found to have developed proteinuria (1 mg protein/ml urine). Once proteinuria was detected the mice were assigned either the control diet or 0.5% conjugated linoleic acid for the remainder of their life. The total number of mice on the dietary treatments were 15 for control diet and 15 for the CLA diet. Protocols for animal care and use were approved by the Research Animal Resources Center of University of Wisconsin-Madison.

Feed Intake and Body Weight. Weekly body weight and survival of the mice were recorded from the beginning of the experiment to the time of death.

Urine Collection and Proteinuria Assay. Mouse urine was collected by using metabolic cages every other week before 28 weeks of age and weekly thereafter. Each mouse was housed in a single metabolic cage for 3 hours to collect urine. A 20 $\mu$l urine sample was diluted four times with distilled water. In a 96 well plate, 20 $\mu$l of diluted urine sample was placed in a well, and 200 $\mu$l of diluted Bio-Rad protein assay reagent was then added to each well. Plates were mildly shaken for 5 min and the color reactions were read at 600 nm with a microtiter plate reader (Autoreader EL310, Bio-tek Instrument). Duplicate samples were applied in microtiter plates and bovine albumen was used as positive control and also to create a standard curve.

Statistical Analysis. Body weight and survival days were compared by Student's t-test to determine the treatment effect. Positive proteinuria ratio was analyzed by Fisher's exact test using a SAS computer program version 5.

Results

Body weight and proteinuria were monitored until the animals died. On average, animals switched to the CLA diet lived 55% longer than those remained on the control diet ($p<0.05$). In addition, the animals who remained on the control diet lost 35% more body weight than those animals that were switched to the CLA diet ($p<0.05$).

We claim:

1. A method for extending the survival time of a human or non-human animal having a disease characterized by autoimmune complexes, the method comprising the steps of:
    detecting autoimmune complexes in the animal; and
    administering to the animal after detecting the autoimmune complexes an amount of conjugated linoleic acid effective to extend the survival of the animal.

2. The method of claim 1, wherein the animal is selected from the group consisting of a human or non-human primate, a mammal, a rodent and a bird.

3. The method of claim 1, wherein the animal is a human.

4. The method of claim 1, wherein the animal has lupus.

5. The method of claim 1, wherein the animal has systemic lupus erythematosus.

6. The method of claim 1, wherein the animal has proteinuria.

7. A method for extending the survival time of a human or non-human animal having nephritis, the method comprising the steps of:
    detecting symptoms of nephritis in the animal; and
    administering to the animal after detecting the nephritis symptoms an amount of conjugated linoleic acid effective to extend the survival time of the animal.

8. The method of claim 7, wherein the animal is selected from the group consisting of a human or non-human primate, a mammal, a rodent and a bird.

9. The method of claim 7, wherein the animal is a human.

10. The method of claim 7, wherein the animal has lupus.

11. The method of claim 7, wherein the animal has systemic lupus erythematosus.

12. The method of claim 7, wherein the animal has proteinuria.

13. A method for reducing body weight wasting of a human or non-human animal having a disease characterized by autoimmune complexes, the method comprising the steps of:
    detecting autoimmune complexes in the animal; and
    administering to the animal after detecting the autoimmune complexes an amount of conjugated linoleic acid effective to reduce the body weight wasting of the animal.

14. The method of claim 13, wherein the animal is selected from the group consisting of a human or non-human primate, a mammal, a rodent and a bird.

15. The method of claim 13, wherein the animal is a human.

16. The method of claim 13, wherein the body weight wasting is reduced by at least 10%.

17. The method of claim 13, wherein the animal has lupus.

18. The method of claim 13, wherein the animal has systemic lupus erythematosus.

19. The method of claim 13, wherein the animal has proteinuria.

* * * * *